(12) United States Patent
Jeppesen

(10) Patent No.: US 7,311,103 B2
(45) Date of Patent: Dec. 25, 2007

(54) METHOD FOR TREATING OBSTRUCTIVE SLEEP APNEA SYNDROME

(75) Inventor: John C. Jeppesen, Ventura, CA (US)

(73) Assignee: Checkmate Holding Company, LLC, Ventura, CA (US)

( * ) Notice: Subject to any disclaimer, the term of this patent is extended or adjusted under 35 U.S.C. 154(b) by 88 days.

(21) Appl. No.: 10/629,511

(22) Filed: Jul. 29, 2003

(65) Prior Publication Data

US 2005/0022821 A1 Feb. 3, 2005

(51) Int. Cl.
*A61F 5/56* (2006.01)

(52) U.S. Cl. ............... 128/201.26; 128/207.18; 128/204.18; 128/848; 128/DIG. 26; 433/32

(58) Field of Classification Search ........... 128/207.18, 128/848, 200.24, 207.14, 200.29, 204.18, 128/206.29, 859–863; 433/32; 600/554, 600/590

See application file for complete search history.

(56) References Cited

U.S. PATENT DOCUMENTS

| | | | | | |
|---|---|---|---|---|---|
| 2,776,486 | A | * | 1/1957 | Manczur | 433/35 |
| 4,472,140 | A | * | 9/1984 | Lustig | 433/38 |
| 4,676,257 | A | * | 6/1987 | Halpern | 607/134 |
| 4,782,832 | A | | 11/1988 | Trimble et al. | 128/207.18 |
| 4,782,837 | A | * | 11/1988 | Hogan | 607/47 |
| 5,018,533 | A | * | 5/1991 | Hawkins | 128/848 |
| 5,117,816 | A | * | 6/1992 | Shapiro et al. | 128/200.24 |
| 5,365,945 | A | * | 11/1994 | Halstrom | 128/848 |
| 5,477,852 | A | * | 12/1995 | Landis et al. | 128/207.18 |
| 5,752,510 | A | * | 5/1998 | Goldstein | 128/207.18 |
| 5,823,193 | A | * | 10/1998 | Singer et al. | 128/848 |
| 5,983,892 | A | * | 11/1999 | Thornton | 128/201.26 |
| 6,012,455 | A | * | 1/2000 | Goldstein | 128/207.18 |
| 6,209,542 | B1 | * | 4/2001 | Thornton | 128/206.29 |
| 6,571,798 | B1 | * | 6/2003 | Thornton | 128/206.21 |
| 7,101,178 | B2 | * | 9/2006 | Diesso | 433/37 |
| 2004/0096801 | A1 | * | 5/2004 | Tucker et al. | 433/38 |
| 2004/0115139 | A1 | * | 6/2004 | Katz et al. | 424/50 |

OTHER PUBLICATIONS

"Vent and Saliva Shield" brochure (1 page), Airway Management Inc., Dallas, TX.
Thornton Adjustable Positioner Triple Laminate (TAP TL) brochure (1 page), Airway Management Inc., Dallas, TX.
No title, Parts list with illustrations (1 page), Comfort Acrylics, Inc., Camas, WA.
"Snoring & Sleep Apnea Solutions" brochure (1 page), Comfort Acrylics, Inc., Camas, WA.
Sleep Apnea Management System (SAAMS), internet webpage found at http://www.quietsleep.com/.

* cited by examiner

*Primary Examiner*—Justine R. Yu
*Assistant Examiner*—Shumaya Ali
(74) *Attorney, Agent, or Firm*—Ralph D. Chabot

(57) ABSTRACT

The invention describes a method for treating Obstructive Sleep Apnea Syndrome (OSAS) utilizing positive airway pressure (PAP) by creating a single-piece, dual arch airway orthotic, using said orthotic to obturate the oral cavity via an acrylic seal between the upper and lower dental arches, retaining the upper and lower dental arches in elastomeric material via a snap-fit and applying PAP via the nasal passages from tubing which is supported from said airway orthotic.

16 Claims, 2 Drawing Sheets

METHOD FOR TREATING OBSTRUCTIVE SLEEP APNEA SYNDROME

BACKGROUND OF THE INVENTION

Obstructive Sleep Apnea Syndrome Syndrome (OSAS) is a serious medical condition that is difficult to treat easily and effectively. The condition is marked by a partial or complete closure of the upper airway during sleep.

There are four basic therapeutic modalities in the treatment of OSAS: pneumatic splinting of the airway with positive airway pressure (PAP), airway orthotic (AO) which mechanically dilates the upper airway, surgery, and combination therapy which uses an airway orthotic plus positive airway pressure.

PAP acts as a pneumatic splint which literally blows open the upper airway during sleep such that the tendency for the upper airway to collapse is either eliminated or reduced.

There are a variety of surgeries to treat OSAS, some approaches work better than others. Since this is not the subject of this patent, nothing further will be said on this issue.

Combination therapy typically utilizes mechanical or physical tissue manipulation of the muscles of the upper airway via use of an AO plus pneumatic splinting of the airway. Alternatively, combination therapy may use an AO without mechanical dilation of the upper airway. When an AO is used without mechanical dilation of the upper airway, the AO may be utilized to stabilize an application device for delivery of PAP with a non-claustrophobic interface and the active treatment then depends solely on pneumatic splinting of the upper airway.

Standard PAP therapy usually includes a nasal application device for delivery of the positive airway pressure to the patient's nasal passages. There are different styles of nasal application devices. These include:
 a) Triangular-shaped nasal masks which form a seal surrounding the patient's nose on his facial surface,
 b) Full-face masks that form a seal on the patient's face around both the nose and mouth,
 c) Nasal inserts commonly referred to as nasal pillows.

The nasal application device is connected to a Continuous Positive Airway Pressure machine (CPAP) via tubing. These air pressure machines (CPAP) can be set to certain and particular pressure settings. Each patient will have a certain and particular pressure level of PAP that will dilate and pneumatically splint his upper airway. When utilized properly, this therapy is very effective in treating the patient with a nocturnally obstructed airway.

Nasal CPAP is considered to be the gold standard in treatment of moderate to severe OSAS. However, this life saving therapy is fraught with significant compliance problems. Clinical studies indicate that compliance on nasal CPAP is less than 50%. Reasons for this non-compliance are numerous and include problems with mask fit and resultant mask discomfort, mask leakage of PAP, claustrophobia, head gear discomfort, head strap discomfort, sleep position (supine) confinement, mouth venting or leakage, chin strap confinement and discomfort, dermatitis, swallowing of air, pressure-related tolerance issues etc.

Airway Orthotics (AO) are oral appliances that are worn in the mouth at night for the purpose of treating OSAS. Historically, there are two basic types of airway orthotics: the tongue retention device (TRD) and the mandibular advancement device (MAD). For the purposes of this disclosure nothing more will be said about the TRD other than to note its existence.

Most mandibular advancement (MADs) devices mechanically dilate the upper airway by moving the lower jaw, or mandible, forward in controlled increments. The airway is dilated by a combination of: pulling the tongue base anteriorly away from the airway and holding it forward during sleep, tightening of the apneic patient's upper airway via anterior and superior movement of the hyoid bone which stretches the infrahyoid muscles attached to the upper airway, innervation of key airway muscle groups such as the genioglossus, palatoglossus, and inferior bellies of the lateral pterygoid(s), and lateral stretching of the hypopharynx.

Mandibular advancement devices can either be fixed or adjustable. In general, adjustable MADs are preferred by most clinicians who treat OSAS because they may be titrated, or gradually adjusted, according to the patient's airway needs. These MAD devices incorporate a variety of different designs and schemes to move the lower jaw forward.

However, advancing of the mandible can result in unpredictable occlusal (bite) changes. Therefore, the clinician must weigh all possible outcome factors, both positive and negative, in formulating his treatment plan.

Mandibular advancing devices, while often helpful, can complicate issues for the patient undergoing "combination therapy." Complicating issues can compromise the effectiveness of the therapy by resulting in decreased compliance or utilization. Therefore, there is a need to create simple and effective therapies for OSAS that minimize complications. Often, the effectiveness of nasal CPAP, airway orthotics, or combination therapy relates to patient compliance with the therapy. Simpler, less burdensome therapies will generally lead to higher compliance and resultant efficacy in treatment.

SUMMARY OF THE INVENTION

The objectives of this invention are to improve on the concept of combination therapy for OSAS based on several factors.
 1) Simplifying the use by the patient to increase compliance through minimization of necessary parts in design of the airway orthotic;
 2) Accommodation of varying nare-to-nare and nose widths for use of nasal pillows and tubing;
 3) Obturation of the oral cavity preventing mouth venting of PAP without the need for a chin strip or need to add a separate piece known as a "vent or saliva shield;"
 4) Use of a 3 mm minimum thickness of acrylic for PAP Tubing Retention Platform construction to improve strength, integrity and malleability to customize tubing angulation via application of heat. Usually this heat is applied by a micro torch;
 5) Improving angulation of nasal tubing by closest preferred approximation anterio-posteriorly to positions directly below the nares.
 6) Minimization of occlusal changes in utilization of airway orthotics by building these oral appliances in a neutral-centric mandibular position with no mandibular advancement such that the mandible is in centric relation, centric occlusion or the like.

Design of Airway Orthotic

This invention will introduce a new type of airway orthotic that will simplify insertion, usage, and increase effectiveness for the patient. This airway orthotic serves three primary functions:

a) to obturate or seal off the oral cavity preventing mouth breathing and/or mouth venting of positive airway pressure (PAP);

b) to support application of PAP via nasal pillows directly from the obturator without use of any headgear, straps or chin support to stabilize the nasal seal during movements at night.

c) to hold the upper and lower jaws in a preferred position via use of an elastomeric material without the use of a hook, chin stabilizer, or strap.

Method of Manufacture

1) Individual impressions are made of the upper and lower teeth and master casts are poured in stone or plaster.

2) A bite registration is also recorded which documents the relationship of the mandible to the maxilia in three dimensions and is used by the laboratory to mount the upper and lower casts on an articulator. The bite registration position may be captured either:

a) In neutral centric position, i.e., without mandibular protrusion/advancement; or, b) In a protruded position referred to as mandibular advancement; and c) May vary the caudal or vertical component to make room for the tongue and/or maximize patency of the airway.

3) The airway obturating orthotic is professionally manufactured in the laboratory and is composed of a hard acrylic exterior which is lined with an elastomeric material such that there is a snap fit when the upper and lower teeth are engaged into it. This snap fit via said elastomeric material holds the lower jaw in preferred position without any additional means. Elastomeric materials flex like rubber when pressure is applied as in the case wherein teeth snapfit over the internal surfaces of the appliance.

The following passages will now compare the present invention with prior art specifically referenced to illuminate useful and novel differences between the present invention and the prior art.

By way of reference I direct the reader to U.S. Pat. No. 6,209,542, entitled "Combination face mask and dental device for improved breathing during sleep." Dr. Thornton describes an apparatus consisting of a face mask connected to an oral appliance. The adjustment means allows for positioning of the mask from a first to a second position. The patent describes an oral appliance that has separate upper and lower arch components.

Goldstein U.S. Pat. Nos. 5,752,510 and 6,012,055 teaches of a dual-arch mandibular advancement device that incorporates application of a nasal mask and nasal inserts.

By comparing the referenced prior art the reader will note fundamental differences between the present invention and what is taught by Thornton and also Goldstein.

The airway orthotic or oral appliance in the present invention is intentionally non-adjustable. By utilizing a fixed/non-adjustable appliance the apnea patient avoids the complication of:

a) first inserting the upper arch and then the lower arch and:

b) then hooking them together.

For certain patients, like those patients with a significant mental or developmental impairment or impairment through aging, this joining together of individual components can be challenging. This challenging problem alone can lead to non-compliance and subsequent failure of the therapy.

With the present invention, the patient simply opens his mouth and bites down with the upper and lower teeth simultaneously onto a one-piece, dual arch orthotic in one clean motion. This fixed orthotic contains both the upper and lower arches in one unit lined with an elastomeric material. This simplicity is preferable because it will increase compliance on the therapy, which increases overall effectiveness medically.

There is the problem referred to as mouth venting of PAP. This is where air is blown into the nose and the patient inadvertently opens his mouth while asleep and thereby permits air to be blown out of his mouth, via path of least resistance. This occurs due to insufficient obturation or sealing-off of the oral cavity. This results in inadequate requisite, therapeutic pressure requirements when PAP is required to effectively open or pneumatically splint a patient's upper airway.

With the two-piece, separate component design, as taught by Thornton, there is a significant space between the upper and lower arches. Unfortunately, this allows for PAP to escape at night when the patient is asleep which results in lowering of therapeutic pressure. Attempts to correct this problem with prior art have included adding a chin strap and/or a separate, extra component referred to as a "vent or saliva shield." This vent shield must be added to the multi-component device complicating utilization by patients.

The present invention has no need for a chin strap or a separate vent shield to prevent leakage of requisite PAP. This problem is solved by sealing the upper and lower arches with acrylic to form a PAP obturator. There is no unsealed space between the upper and lower components anteriorly of the airway orthotic from which PAP can escape. Some space posteriorly may be intentionally left open for tongue room without compromising obturation because the tongue will fill the void laterally and complete the obturation. The snap fit of the teeth produced by the elastomeric material obviates the need for a chin strap or similar means to keep the mouth closed at night when PAP is blown into the nasal passages.

Advancing the mandible to correct OSAS can result in untoward occlusal changes or changes in the patient's bite. This occurs from significant orthodontic forces being applied to teeth due to intentional forward positioning of the mandible by using the maxillary teeth as an anchor or fulcrum to lever the mandible forward which results in muscles applying undesirable forces upon teeth at night.

The present invention solves this problem by placing the patient's lower jaw in a neutral centric position to minimize or eliminate orthodontic forces on the teeth where there is clinical indication to do so. However, the present invention may utilize mandibular advancement in the design when there may be some benefit to do so. The only reason to advance the mandible in combination therapy would be an attempt to reduce unreasonably high therapeutic PAP pressure if this factor is reducing patient compliance on nasal CPAP.

Means of application of PAP via the Thornton (combination) invention referred to as the "TAP/SAAMS" uses a one size fits all noses, tubing retention platform (SAAMS). In clinical practice this is very problematic as nose and nare widths vary widely. Without adjusting the width laterally of the PAP Tubing Retention Platform, many patients will fail this type of combination therapy. Thornton's art does not anticipate the use of variable nose-width tubing retention platforms, nor is it obvious to those skilled in the art.

The present invention incorporates a method whereby the PAP Tubing Retention Platform is varied in lateral width to accompany the varied width of patient noses and nares. Different sizes in lateral widths of PAP Tubing Retention Platforms permit proper angulation and placement of nasal tubing carrying PAP. Proper angulation and placement of PAP Tubing results in a profound and stabile seal of PAP at the nares.

The present invention seeks to overcome prior art design that is fraught with another very significant problem as concerns proper angulation of nasal tubing to deliver PAP. This problem is that often the SAAMS platform is simply too far away, anterior-posteriorly, from the patient's nasal passages to approach the nares from a preferred angle. This is because the TAP/SAAMS design attaches or fits directly over the "Front Assembly" utilizing a Sheath Slide Extension. The anterior end of the Front Assembly, where the Adjustable Advancement Nut lies, is normally at least 22 mm from the labial surface of the maxillary anterior teeth. When the SAAMS tubing retention platform is added/ screwed into place on top of the Front Assembly via the Sheath Extensions, the PAP nasal tubing is at least 35 mm from the labial surface of the maxillary anterior teeth. This design flaw forces the clinician to angulate the nasal tubing in an undesirable manner often resulting in failure to properly seal the nares and maintain the seal while the patient is asleep.

The present invention allows the PAP Tubing Retention Platform to slide posteriorly to preferred positions which are much closer to the patient's nares. This allows for preferred positioning and angulation of PAP nasal tubing thereby improving the requisite seal at the nares and thereby increasing success in treatment. The present invention allows for the PAP Tubing Retention Platform to achieve proximity to the labial aspect of the maxillary anterior teeth in a range of 5 mm to 30 mm depending on the patient's anatomy.

In addition to moving the PAP Tubing Retention Platform posteriorly on the Variable Length Slide to achieve proximity of PAP Tubing directly below the nares, the present invention recognizes additional means to assist in solving this problem. First, the PAP Tubing Retention Platform may be "U" shaped a the posterior end of the Platform such that the PAP Tubing Holes swing backward on the left and right sides toward the patient's face. Second, the adjustable Slide Mount Bracket may be mounted anterior to the posterior edge of the PAP Tubing Retention Platform allowing the Platform to get closer to the patient's face.

The present invention also envisions a method of changing the Thornton design whereby this limitation in design, which prevents close approximation of the PAP Tubing Retention Platform to more closely approximate access to the flares, is overcome. By removing the Adjustable Advancer Nut and inserting a female threaded stainless steel sleeve into the posterior section of the Front Assembly, a new Sheath Extension can be fit over this remaining section of the Front Assembly to bring a SAAMS' PAP Tubing retention platform closer to the preferred position underneath the patient's nares. Alternatively, a new Front Assembly could be designed without the Adjustable Advancer Nut that includes a built-in PAP Tubing Retention Slide that could be directly screwed into the Locator Plate allowing closer approximation of the PAP Tubing Retention Platform posteriorly. This would allow the current TAP/SAAMS user to add PAP and reduce distance from the nares by at least 8 mm. This would significantly improve the combination therapy described by Thornton.

The "TAP/SAAMS" design incorporates a metal component termed the "Locator Plate" which is imbedded within the anterior shell of acrylic in the upper arch component of the TAP device. The Front Assembly with Adjustable Advancer Nut is screwed into this Locator Plate via the Locator Nut Set. On top of this is the platform Sheath Extension that in turn screws onto the end of the Adjustable Advancer Nut. Because the Locator Plate is imbedded into the acrylic it can sustain excessive forces due to levering action of the Sheath Extension Slide such that there is a tendency for fracture of the acrylic at the anterior surface of the upper component of the MAD.

The present invention has no metal parts imbedded within the acrylic of the airway orthotic. The PAP Tubing Retention Platform Slide is bonded, injection molded, or cast in acrylic and thereby attached to the single piece, dual arch obturating airway orthotic. All exterior components are made from acrylic and bonded together. This greatly reduces potential for fracture. Additionally, in the present invention the length of the PAP Retention Platform Slide may be cut once the patient is fitted thereby reducing lever arm forces. This is not possible with the Thornton invention without irreparably damaging it.

This invention also seeks to improve on another nasal insert/pillow pressure application structure device known as the "Adam Circuit." The Adam Circuit is a headgear device sold by Puritan-Bennett Corp. (Pleasanton, Calif.) under the trademark "Breeze" that attempts to stabilize the use of nasal pillows. However, this device described in U.S. Pat. No. 4,782,832 utilizes an uncomfortable and cumbersome headgear to support the sealing of the patient's nares with PAP. This device has a significant tendency to become displaced when a patient moves around in his bed at night or simply shift to his side. When this device is in contact with his bed-pillow the seal at the nares is often broken thereby reducing the requisite therapeutic pressure prescribed to open the patient's upper airway. The present invention utilizes nasal pillows but improves on the method of stabilization of the seal of the nares and avoids the uncomfortable and cumbersome headgear.

In reference to U.S. Pat. Nos. 5,752,510 and 6,012,455 (Goldstein) there are novel and useful differences between the prior art and the present invention.

Goldstein describes an oral appliance that produces a double bite and uses PAP in combination. But there is no intent to obturate the oral cavity and the reason for Goldstein's dual arch is for a different purpose and his method of design and manufacture is quite clearly different than the present invention. The astute reader will note that the differences in the present invention are novel and useful as compared to Goldstein.

DETAILED DESCRIPTION OF THE PREFERRED EMBODIMENT

Figure 1:
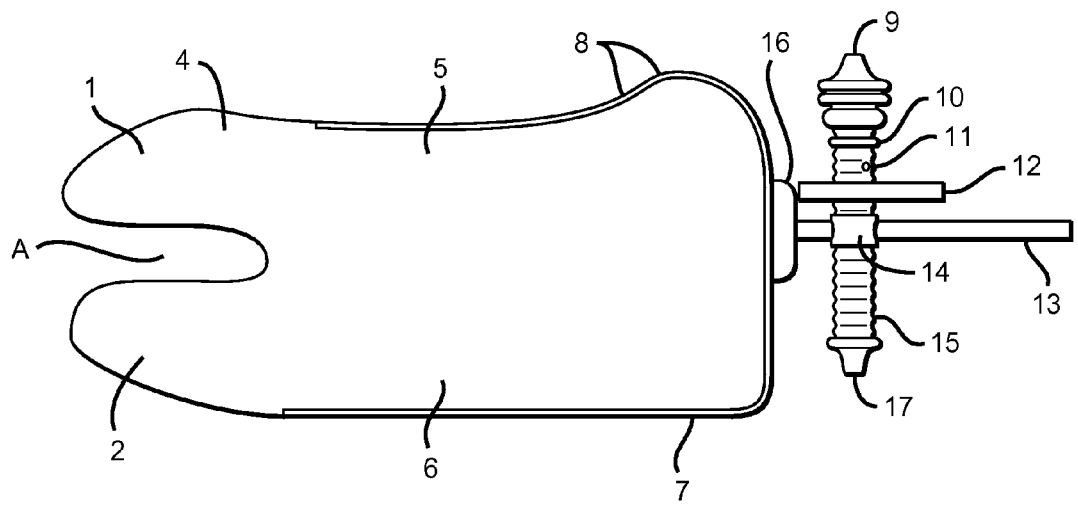
FIG. 1 shows the present invention utilizing a single-piece, dual arch, obturator with an acrylically-connected slide upon which moves an adjustable PAP Tubing Retention Platform device.
Figure 3:
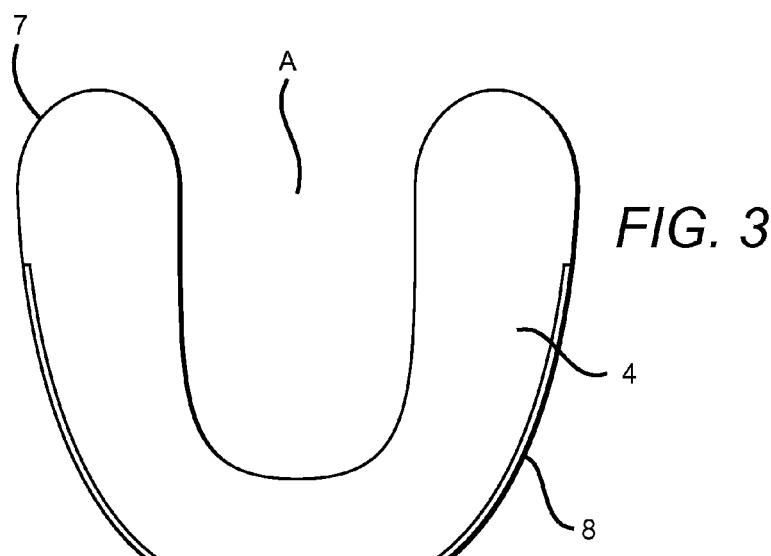
FIG. 3 shows a superior view of the dual arch, obturating airway orthotic with anterior supported for an array of varying width PAP Tubing Retention Platforms. Only one size PAP Tubing Retention Platform is shown in this figure.

FIG. 1 shows a lateral view of the present invention. This view in from the patient's right side where the Upper Right Quadrant 1 is superior and the Lower Right Quadrant 2 is inferior. Posteriorly there is Tongue Space A just where the Solid Acrylic Obturating Seal 8 ends. Typically the Solid Acrylic seal will extend to at least the mesial aspect of the maxillary first molar if not slightly further to create the most robust seal. The Upper Dental Arch 5 is superior to the Lower Dental Arch 6. The airway orthotic is composed of Exterior Hard Acrylic 7 and is lined interiorly with Elastomeric Material 4. Anteriorly the 5 mm Slide Mount 16 is operatively connected to the Variable Length Slide 13. Upon the Variable Length Slide the Variable Width PAP Tubing Retention Platform 12 is adjustably affixed to the Variable Length Slide via the Slide Mount Bracket 14. Superiorly and anteriorly there is a Nasal Pillow 9 which fits over a Collar 10. The Collar inserts into the PAP Tubing 15 which is threaded through the Variable Width PAP Tubing Retention Platform via the PAP Tubing Hole (FIG. 3, 18). At a certain preferred distance from the nose inferiorly is a Whisper Swivel II Valve (Respironics Part Number 332113). Above the Whisper Swivel II Valve and within the PAP Tubing is located an optional Exhaust Port 11. Both the Whisper Swivel II Valve and the Exhaust Port are utilized to blow off or vent Carbon Dioxide ($CO_2$) on patient exhalation. The rate of expiratory flow from use of these structures is between 5-15 liters per minute. The need for the optional Exhaust Port can be determined in the sleep laboratory by end tidal $CO_2$ monitoring. If the patient is retaining too much $CO_2$ PAP Tubing Holes are created to assist the Whisper Swivel II Valve in blowing off excess $CO_2$.

Figure 2C:
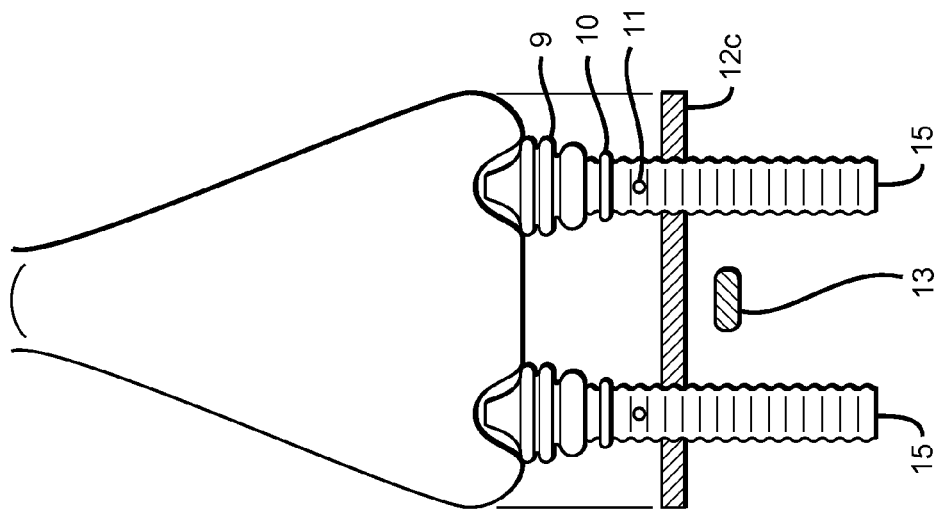
FIG. 2c shows the PAP Tubing Retention Platform adjacent to a large nare and nasal width.
Figure 2B:
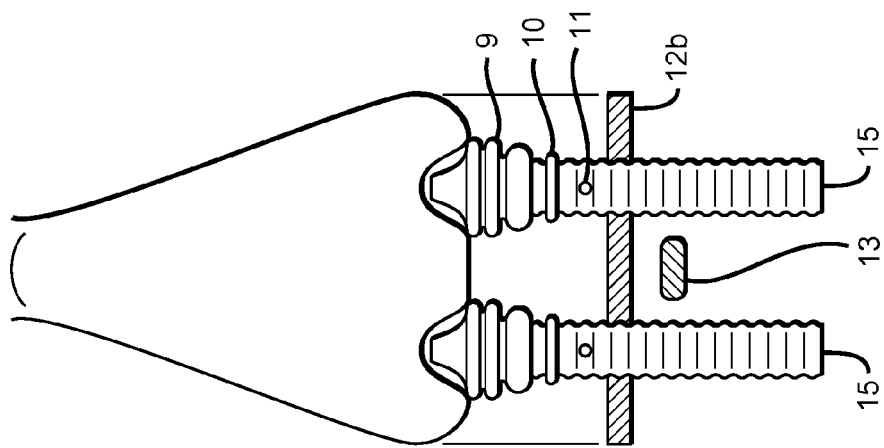
FIG. 2b shows the PAP Tubing Retention Platform adjacent to a medium nare and nasal width.
Figure 2A:
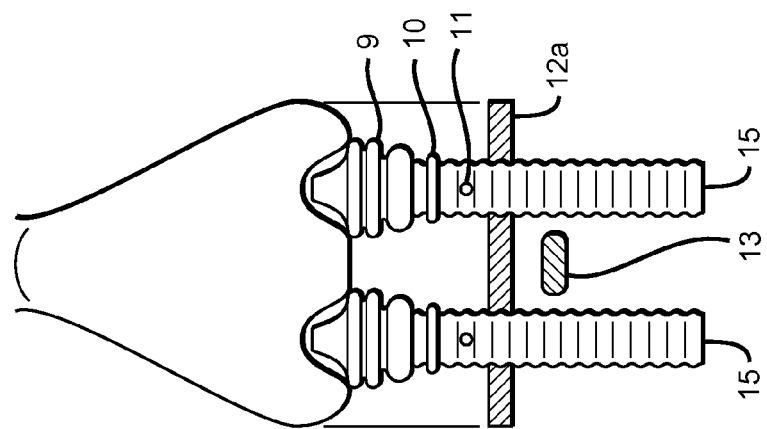
FIG. 2a shows the PAP Tubing Retention Platform adjacent to a small nare and nasal width.

FIG. 2 shows the Present Invention whereby a method of treating Obstructive Sleep Apnea Syndrome utilizes PAP Tubing Retention Platforms that are variable in widths to correspond with variations in nasal and nare width. FIG. 2 shows three hypothetical patient nasal widths small, medium, and large that correspond with particular width PAP Tubing Retention Platforms (small 12a, medium 12b, and large 12c). The reader will note that there could be additional Platforms as necessary to accommodate any and all variations in patient nasal widths. If there is flaring of the nares superiorly the PAP Tubing Retention Platforms may be increased slightly in width to allow for angulation medially of the Platform via application of heat to bend the acrylic so as to customize the angular approach of the PAP Tubing 15. The preferred thickness of the Variable Width PAP Tubing Retention Platforms should be at least 3 mm. These PAP Tubing Retention Platforms can be manufactured via standard methods such as heat "suck-down" whereby a 3 mm sheet of acrylic such as Biocryl is heated until pliable and vacuum-formed onto various width molds forming the preferred structures. They may also be injection molded or cast directly in acrylic via the lost wax technique. The PAP Tubing Retention Platform is mounted onto the Slide 13 via the Slide Mount (FIG. 1) and can be preferably located or adjusted as close as 5 mm from the labial surface of the anterior teeth. The preferred range of location of the PAP Tubing 15 will be 5 mm to 30 mm from the labial surface of the maxillary anterior teeth. Once the preferred location anterio-posteriorly is located for the individual patient the Slide 13 may be cut to reduce unnecessary lever arm forces.

Figure 3A:
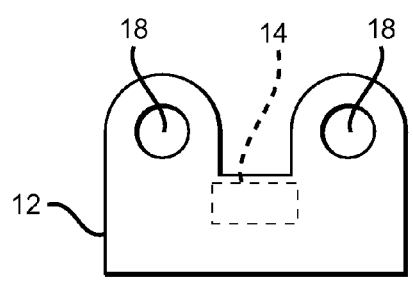
FIG. 3a is a tor view of the PAP Tubing Retention Platform.

FIG. 3 shows the present invention in a superior view and FIG. 3a is a tor view of the PAP Tubing Retention Platform 12. The Variable Width PAP Tubing Retention Platform 12 is shown in two widths and styles in this figure and is mounted onto the Variable Length Slide 13 via the Slide Mount Bracket 14. The first style is rectangular and the second style is "U" shaped. There are two PAP Tubing Holes 18 which correspond to the right and left nares in both styles. The width of the PAP Tubing Retention Platform and position of the holes is preferably selected to match the corresponding width of the patient's nasal and nare width. The Solid Acrylic Obturating Seal 8 continues from the anterior region of the airway orthotic posteriorly as necessary to seal off the oral cavity from loss of requisite therapeutic positive airway pressure as determined in the sleep laboratory. There is Tongue Space A anteriorly, laterally, and vertically. The vertical or caudal dimension of the airway orthotic is varied according to tongue size and is determined by the experienced clinician through a variety of means or methods. The preferred embodiment utilizes a neuromuscular TENS (Transcutaneous Electrical Nerve Stimulation) technique whereby the masticatory muscles are profoundly relaxed to proper working lengths via this pulsing technique placing the mandible in three dimensional harmonious space position with respect to the maxilla. In this manner the mandibular position anterio-posteriorly (AP) and vertically is determined by the muscles themselves rather setting an arbitrary position. This neuromuscularly-determined position is referred to earlier in the specification as "neutral centric" position. If the need presents, due to excessive therapeutic PAP requirements for an individual patient, the AP position of the mandible may be somewhat protruded forward so as to create some mechanical dilation of the upper airway. However, this forward positioning of the mandible will increase the risk of a deleterious change in the patient's occlusion or bite. Therefore, the preferred position will typically be the neutral centric position as determined by the experienced clinician.

The foregoing description of the preferred embodiments of the invention has been presented for the purposes of illustration and description. It is not intended to be exhaustive or to limit the invention to the precise form disclosed. Accordingly, the foregoing description should be regarded as illustrative rather than restrictive, and it should be appreciated that variations may be made in the embodiments described by workers skilled in the art without departing from the scope of the present invention as defined by the following claims.

What is claimed is:

1. The method of applying positive airway pressure (PAP) to nasal passages of a patient for the purpose of treating Obstructive Sleep Apnea Syndrome (OSAS) without the use of a hook, chin stabilizer, or chin strap comprising the steps of:
    a. fabricating a dual arch oral appliance for obturating the oral cavity of the patient which substantially prevents mouth venting of PAP, said dual arch oral appliance fabricated from dental impressions taken of the patient's upper and lower teeth and where said oral appliance is fabricated to maintain the patient's bite registration in the neutral centric position, said oral appliance further comprising an anterior, extraoral slide affixed thereto;
    b. positioning said oral appliance within a patient's mouth where said oral appliance is aligned with the patient's upper and lower dental arches to maintain the patient's mandible in a substantially neutral centric position without protrusion of the mandible;

c. providing a pair of PAP tubing and connecting one distal end of each of said tubing to an external source of positive airway pressure;

d. mounting a PAP Tubing Retention Platform to said slide for slidable movement along said slide, said PAP tubing operatively connected to said PAP Tubing Retention Platform;

e. slidably displacing said PAP Tubing Retention Platform along said slide to a position optimum for inserting each of said pair of tubing into a respective nasal cavity;

f. inserting the other end of each tubing into a respective nasal cavity for delivery of air from said external source; and, g. sealing the patient's nares with nasal pillows.

2. The method of claim 1 further comprising the positioning of said PAP Tubing Retention Platform and said PAP tubing s anterior-posteriorly to a position within a range of 5 mm to 30 mm from the labial surface of the maxillary anterior teeth.

3. The method of claim 1 wherein said PAP Tubing Retention Platform is composed of an acrylic material that is at least 3 mm thick.

4. The method of claim 3 wherein said acrylic material can be adjusted to optimize the desired angulation via application of heat.

5. The method of claim 1 wherein said PAP Tubing Retention Platform is created via injection molding.

6. The method of claim 1 where said obturator comprises an exterior surface made from an acrylic material lined with an elastomeric material.

7. The method of claim 1 wherein said anterior extraoral slide is acrylically bonded to the anterior surface of said oral appliance without the use of metal parts.

8. The method of claim 1 where said oral appliance is composed of a hard exterior acrylic and deposited with an elastomeric material.

9. The method of claim 1 where said oral appliance is fabricated from a three-dimensional bite registration for orienting the position of the upper and lower dental arches.

10. The method of claim 9 where said bite registration is produced utilizing Transcutaneous Electrical Nerve Stimulation (TENS).

11. The method of claim 1 further comprising the step of selecting an appropriate size PAP tubing Retention Platform to conespond to the patient's nasal width.

12. A method for treating a patient with Obstructive Sleep Apnea Syndrome (OSAS) comprising the steps of:

providing a dual arch oral appliance for placement substantially within the oral cavity of a patient, said dual arch oral appliance fabricated from dental impressions taken of the patient's upper and lower teeth and where said oral appliance is fabricated to maintain the patient's mandibular and maxillary arches in a neutral centric position and designed to substantially obturate the patient's oral cavity and prevent venting of air through the oral cavity;

providing a retention platform operably but not integrally connected to said oral appliance for positioning anteriorially of the patient's mouth, and a pair of air supply tubes retained by said retention platform;

positioning said dual arch oral applicance within a patient's oral cavity;

engaging one arch of the oral appliance to the patient's mandibular arch and the other arch of the oral appliance to the patient's maxillary arch by the patient closing said oral cavity, said engagement, without protrusion of the mandible, and locating the mandibular arch in a neutral centric position with respect to the maxillary arch;

positioning the end of each tube within a respective nostril;

connecting the distal ends of each of said tubes to an air supply source; and, delivering an air flow to the patient from said air supply source, through said pair of tubes.

13. The method of claim 12 further comprising the steps of supporting and stabilizing tubes connected to said dual arch oral appliance.

14. The method of claim 13 comprising the additional steps of selecting a PAP Tubing Retention Platform appropriately sized for said patient's nasal features, connecting said tubes to said PAP Tubing Retention Platform, and sealing both patient's nares, each nare sealed using a nasal pillow operably connected to a portion of respective tubing positioned within a nostril.

15. The method of claim 12 additionally comprising the step of obtaining a three-dimensional bite registration in a neutral centric position via Transcutaneous Electrical Nerve Stimulation (TENS).

16. A method for treating a patient with Obstructive Sleep Apnea Syndrome (OSAS) while comprising the steps of:

obtaining from the patient a three-dimensional bite registration where the patient's mandibular arch and maxillary arch are in a neutral centric position by relaxing the patient's facial muscles using Transcutaneous Electrical Nerve Stimulation (TENS);

fabricating a dual arch oral appliance for obturating the oral cavity of the patient, utilizing said three-dimensional bite registration, which substantially prevents mouth venting of PAP, where said oral appliance is fabricated to maintain the patient's mandibular arch and maxillary arch in the neutral centric position;

providing a retention platform operably connected to said dual arch oral appliance for positioning anteriorially of the patient's mouth, and a pair of air supply tubes retained by said retention platform, each of said tubes having an end with a nasal pillow coupled thereto, wherein the operable connection of the retention platform to the dual arch oral appliance comprises an elongated anterior slide extending away from said dual arch oral appliance, and where said retention platform is slidably mounted to said slide;

positioning said dual arch oral applicance within a patient's oral cavity;

engaging one arch of the oral appliance to the patient's mandibular arch and the other arch of the oral appliance to the patient's maxillary arch by the patient moving his mandibular arch towards the maxillary arch, said engagement causes the mandibular arch and maxillary arch to be positioned in a substantially neutral centric position;

positioning said end of each tube within a respective nostril of the patient;

connecting the distal ends of each of said tubes to an air supply source; and, delivering an air flow to the patient from said air supply source, through said pair of tubes.

* * * * *